United States Patent
Chen et al.

[11] Patent Number: 6,129,848
[45] Date of Patent: Oct. 10, 2000

[54] METHOD FOR CONTINUOUS MAGNETIC SEPARATION OF COMPONENTS FROM A MIXTURE

[75] Inventors: Ching-Jen Chen; Yousef Haik; Vinay M. Pai, all of Tallahassee, Fla.

[73] Assignee: The Florida State University, Tallahassee, Fla.

[21] Appl. No.: 09/461,586

[22] Filed: Dec. 16, 1999

Related U.S. Application Data

[62] Division of application No. 09/027,084, Feb. 20, 1998, Pat. No. 6,036,857.

[51] Int. Cl.[7] ............................ B01D 35/06; G01N 33/553
[52] U.S. Cl. ........................ 210/695; 209/213; 209/223.1; 210/738; 210/749; 435/2; 435/7.2; 435/7.21; 436/526
[58] Field of Search ..................... 209/213, 223.1; 210/208, 222, 695, 738, 749; 422/101; 435/2, 7.2, 7.21; 436/526

[56] References Cited

U.S. PATENT DOCUMENTS

| | | |
|---|---|---|
| 4,251,372 | 2/1981 | Dolle . |
| 4,508,625 | 4/1985 | Graham . |
| 4,672,040 | 6/1987 | Josephson . |
| 4,816,143 | 3/1989 | Vollmar . |
| 4,910,148 | 3/1990 | Sorensen et al. . |
| 4,935,147 | 6/1990 | Ullman et al. . |
| 4,946,603 | 8/1990 | Laugharn et al. . |
| 4,988,618 | 1/1991 | Li et al. . |
| 5,089,128 | 2/1992 | Garaschenko et al. . |
| 5,254,248 | 10/1993 | Nakamura . |
| 5,409,813 | 4/1995 | Schwartz . |
| 5,458,785 | 10/1995 | Howe et al. . |
| 5,514,340 | 5/1996 | Lansdorp et al. . |
| 5,536,475 | 7/1996 | Moubayed et al. . |
| 5,541,072 | 7/1996 | Wang et al. . |
| 5,558,839 | 9/1996 | Matte et al. . |
| 5,567,326 | 10/1996 | Ekenberg et al. . |
| 5,622,831 | 4/1997 | Liberti et al. . |
| 5,882,514 | 3/1999 | Fletcher . |

FOREIGN PATENT DOCUMENTS

| | | |
|---|---|---|
| 0 672 458 | 9/1995 | European Pat. Off. . |
| 2 300 258 | 10/1996 | United Kingdom . |
| WO 91 04059 | 4/1991 | WIPO . |

*Primary Examiner*—David A. Reifsnyder
*Attorney, Agent, or Firm*—Reed Smith Shaw & McClay, LLP

[57] ABSTRACT

A magnetic system and apparatus having a multi-dimensional gradient for continuous, on-line separation of components from a mixture of chemical entities which comprises at least one separation chamber with a plurality of channels and a plurality of magnets, and a method is provided for continuously and magnetically separating and treating components of a mixture of chemical entities using a multi-dimensional gradient.

35 Claims, 6 Drawing Sheets

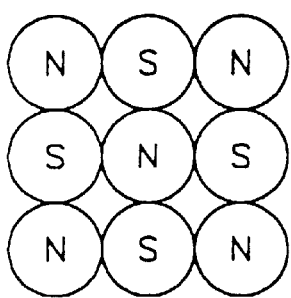
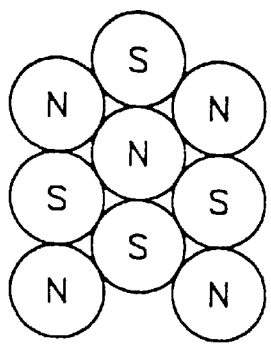
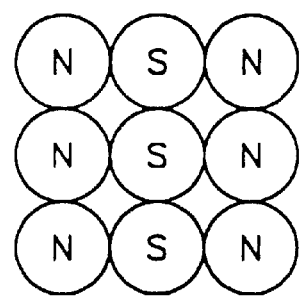
*Fig. 6(a)*  *Fig. 6(b)*  *Fig. 6(c)*
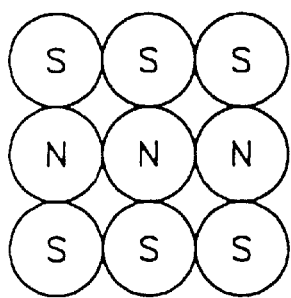
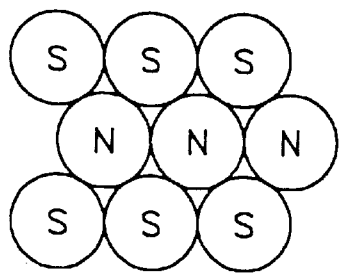
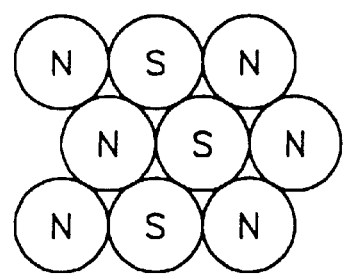
*Fig. 6(d)*  *Fig. 6(e)*  *Fig. 6(f)*
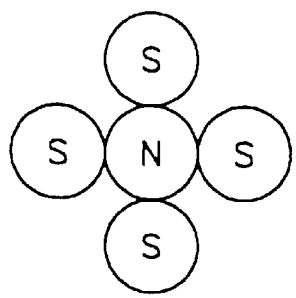
*Fig. 6(g)*

METHOD FOR CONTINUOUS MAGNETIC SEPARATION OF COMPONENTS FROM A MIXTURE

CROSS-REFERENCES TO RELATED APPLICATIONS

This application is a division of U.S. application Ser. No. 09/027,084, filed Feb. 20, 1998, now U.S. Pat. No. 6,036,857.

FIELD OF THE INVENTION

The present invention relates to a magnetic system and apparatus having a multi-dimensional gradient for the continuous, on-line separation of components from a mixture of chemical entities. The system and apparatus of the present invention can be used specifically to separate blood components from a whole blood sample. The invention also relates to a method of continuously and magnetically separating a component from a mixture of chemical entities using a multi-dimensional gradient, and a method of manufacturing a continuous magnetic separation apparatus.

BACKGROUND OF THE INVENTION

The separation and isolation of blood components from a whole blood sample is a significant aspect of the treatment and clinical and laboratory testing of such blood components. There are numerous methods and apparati for the separation of blood components.

Whole blood can be separated by low speed centrifugation into a cell free fluid called serum (or if a blood anticoagulant is present) and a pellet containing cells and platelets. Serum is about 92% water and contains electrolytes, lipoproteins, proteins, hormones, other nutrients and vitamins. The lipoproteins are lipid-protein complexes. Lipoproteins are the primary transport molecules for lipids and also transport vitamin E and beta-carotene (provitamin A). Lipoproteins are further divided into very low density lipoprotein, low density lipoprotein and high density lipoprotein. High levels of low density lipoprotein are associated with atherosclerosis and cardiovascular disease. In contrast, high levels of high density lipoprotein are thought to protect against atherosclerosis.

The primary proteins found in plasma are albumin, globulins, fibrinogen. Albumin is the most abundant plasma protein (about 60%) and is a carrier molecule for nonesterified fatty acids. Albumin also plays a role in maintaining the osmotic pressure of blood. The globulins are further divided into alpha-, beta-, and gamma-globulins. The gamma-globulin fraction contains molecules that function as antibodies in the humoral immune system. Fibrinogen functions in clot formation.

The red blood cell (or erythocyte) is the primary cell found in blood. This unique cell has a membrane but no other membranous organelles and does not have a cell nucleus. The primary function of red blood cells is oxygen transport to tissues and the removal of carbon dioxide. The oxygen carrying molecule in the red blood cell is hemoglobin. The red blood has a biconcave shape and is extremely deformable and able to move through very small capillaries. In anemia, the number of red blood cells in a given volume of blood is low resulting in a decreased ability to deliver oxygen to tissues. Nutritional and/or genetic factors can contribute to anemia.

Blood also contains white blood cells and platelets. White blood cells (or leukocytes) include monocytes, lymphocytes, neutrophils, eosinophils, and basophils. Neutrophils, eosinophiles, and basophils (all three are also called granulocytes) as well as monocytes are phagocytic cells. Phagocytic cells and lymphocytes play a key role in the immune system. Platelets function in clot formation.

Since blood components have magnetization properties, there have been numerous efforts to utilize magnetism to separate and isolate such blood components. The most common problems with the prior art is that they cannot perform the separation in a continuous manner and they do not use a multi-dimensional gradient. In addition, the prior art does not provide a decoupling process and some of the prior art conduct separation in a static stage rather than a constant flow stage.

U.S. Pat. No. 4,910,148 to Sorenson et al. relates to a method and device for separating magnetized particles from biological fluids, particularly white blood cells using a monoclonal antibody to link the cells to magnetic beads. In contrast to the present invention, the Sorenson separation is static (i.e., no flow) and is conducted in a plastic blood bag. The magnetic beads are linked to the cancer white cells by an agitation process and then a magnetic field is applied to keep the white blood cells with the magnetic beads in the disposable plastic bag. The Sorenson device also requires space between the magnets which does not optimize the magnetic gradient (magnetic force). The back plate of the Sorenson device is a soft magnetized material and the magnets are Samruim-Cobalt. Sorenson has a volume limitation since it uses a blood bag (150 ml) and there is no decoupling between the beads and the white blood cells. Matter of fact, the cells remain in the disposable blood bag after separation.

U.S. Pat. No. 5,514,340 to Lansdorp, et al. relates to a device for separating magnetically labeled cells in a sample using an applied magnetic field. Lansdorp uses magnetized screens to attract the magnetic particles allowing the biological fluid to be caught in the magnetic wires of the screen. The magnets used in Lansdorp must constantly be cleaned since there is contact between the magnets and the blood cells.

U.S. Pat. No. 5,567,326 to Ekenberg et al. relates to an apparatus and methods for separating magnetically responsive particles from a non-magnetic test medium in which the magnetically responsive particles are suspended. In Ekenberg, small patch amounts of biological fluid are placed in a tube then a magnetic pin is inserted in the fluid for separation.

U.S. Pat. No. 5,541,072 to Wang et al. relates to methods and devices for separation of magnetic particles and/or magnetic-associated substances from non-magnetic associated substances and media. Unlike the present invention, the Wang method does not utilize the optimum magnetic gradient (magnetic force) available since Wang situates its magnets on two opposing sides.

U.S. Pat. No. 4,988,618 to Li et al. relates to a magnetic separation device for use in immunoassay or hybridization assay procedures. The Li device comprises a base having a plurality of orifices for receiving nonferrous containers which hold the sample and the assay components including ferrous particles. The orifices are surrounded by a plurality of magnets which are spaced about the peripheral of the orifices.

U.S. Pat. No. 4,935,147 to Ullman et al. relates to a method for separating a substance from a liquid medium, particularly applicable for cells and microorganisms from aqueous suspension and also for the determination of a analyte. Although Ullman discusses a method with a reversible non-specific coupling, the method is not continuous nor does it utilize a multi-dimensional gradient.

The presently claimed invention overcomes the above mentioned problems by providing a system, an apparatus and a method for continuous separation of components from a mixture of chemical entities using a multi-dimensional gradient.

SUMMARY OF THE INVENTION

Accordingly, the object of the present invention is to provide a magnetic system and apparatus having a multi-dimensional gradient for continuous, on-line separation of components from a mixture of chemical entities.

Another object of the present invention is to provide an apparatus and system for continuous, on-line magnetic separation of blood components from a whole blood sample.

Yet another object of the invention is to provide a method for continuously and magnetically separating a blood component from a mixture of chemical entities utilizing a multi-dimensional gradient.

A further object of the present invention is to provide a method of manufacturing a continuous magnetic blood separating apparatus.

Still another object of the present invention is to provide a system and a method for a continuous magnetic separation of blood components from a whole blood sample using a continuous blood flow and having a decoupling process.

The present invention relates to a magnetic system having a multi-dimensional gradient for continuous, on-line separation of components from a mixture of chemical entities. The system comprising: (a) at least one mixing chamber for agitating the mixture and magnetic particles, the particles being attached to the components of the mixture upon agitation, and (b) at least one separation chamber. The separation chamber comprises a plurality of magnets and a plurality of channels having an inlet and an outlet. The magnets are arranged on one side of the channels and are in contact with one another to create a magnetic field. The mixture containing the particle attached components are introduced into the inlet of the channels of the separation chamber, and the magnetic field of the magnets captures the particle attached components within the channels and the remaining mixture exits the outlet of the channels of the separation chamber.

In another embodiment of the invention, the magnetic system further comprises a solution reservoir for introducing solution through the inlet and the channels for flushing out the particle attached components through the outlet of the channels of the separation chamber upon deactivation of the magnetic field. The magnetic system also comprises a decoupling agent reservoir for introducing a decoupling agent to the particle attached components and an additional mixing chamber for agitating the decoupling agent and the particle attached components allowing the separation of the particles and the components. In one embodiment, the decoupling agent attaches to the components and the magnetic particles deattach. The decoupling agent attached components and particle mixture are reintroduced into the separation chamber and the magnets are reactivated to produce the magnetic field which captures the magnetic particles and the remaining decoupling agent/components exit the outlet of the channel of the separation chamber. The separation of the components and magnetic particles can be done in numerous ways. Adjusting the temperature or pressure can physically separate the components and particles. Decoupling agents such as sugar, salt or pH changes can be used to chemically separate the components and particles.

The magnetic system can also comprise a treatment device for treating the remaining mixture; a collection chamber for reintroducing the components to the treated mixture; and a plurality of directional valves for controlling the flow of the mixture, components, solutions and decoupling agent.

In one embodiment, the separation chamber of the magnetic system can further comprise a bed for supporting the magnets. The preferred material for the bed is a soft magnetic iron metal.

The magnets can be any high energy rare earth magnets such as NdFeB or SmCo magnets. Each of the magnets has an axis with opposing north and south poles, one of the poles rests on the bed and the other pole faces the plurality of channels. Each of the magnets are aligned side-by-side to the other magnets. The axis of each of the magnets is perpendicular to the bed. In another embodiment, the axis of each of the magnets is parallel to the axis of the other magnets and perpendicular to the channels.

The mixture of chemical entities can be a whole blood sample and the components can be any biological micro-molecule such as red blood cells, white blood cells, platelets and other plasma borne components.

In one embodiment, the plurality of magnets can be arranged in alternating magnetic poles so that the magnets are aligned side-by-side with a configuration of north-south-north-south, or are slightly offset from the side-by-side configuration.

In yet another embodiment, the plurality of magnets are vertically aligned in alternating poles so that there is a vertical line of north poles aligned side-by-side with a vertical line of south poles, or are slightly offset from the side-by-side configuration.

In still another embodiment, the plurality of magnets are horizontally aligned in alternating poles so that there is a horizontal line of north poles aligned side-by-side with a horizontal line of south poles, or are slightly offset from the side-by-side configuration.

In a further embodiment, the magnets are arranged so that one magnet having one pole is surrounded by other magnets of opposing poles on four sides.

In one embodiment, each of the channels has varying widths, and the channel width is increased at an entrance near the inlet and the channel width is tapered at an exit near the outlet. The plurality of magnets can also be situated underneath the channel near the inlet and the outlet of the separation chamber. The bed can be tilted on one side in relation to the separation chamber. The tilted side of the bed is in contact with one side of the separation chamber and the untilted side of said bed being from about 0.5 to about 3 cm in distance from the separation chamber.

The magnetic system can further comprise a switching mechanism for bringing the separation chamber in contact with the plurality of magnets and the magnet bed thereby activating the magnetic field produced by the magnets and for distancing the separation chamber from the plurality of the magnets and the bed thereby deactivating the magnetic field. The switching mechanism can include, but is not limited to the following: a plurality of guide rails and electromagnetic coils, rack and pinion, or belt driven mechanism.

The magnetic particles, in one of the embodiments, can be microspheres which are ligand covered and coupling agent bound. The ligand is protein and the coupling agent is lectin.

The present invention also relates to a magnetic apparatus having a multi-dimensional gradient for separation of components from a mixture of chemical entities. The apparatus comprises a separation chamber comprising a plurality of magnets and a plurality of channels having an inlet and an outlet. The magnets are arranged on one side of the channels and are in contact with one another to create a magnetic field. A mixture containing a magnetic particle attached components is introduced into the inlet of the channels of the separation chamber and the magnetic field of the magnets captures the particle attached components within the channels and the remaining mixture exits the outlet of the channels of the separation chamber.

In one embodiment, the separation chamber further comprises a bed for supporting the magnets and the bed is preferably composed of a soft magnetic iron metal. The bed upon which the magnets are set can be flat or staggered.

The magnets are high energy rare earth magnets, and preferably NdFeB or SmCo magnets. Each of the magnets has an axis with opposing north and south poles, one of the poles rests on the magnetic bed and the other pole faces the plurality of the channels, and each of the magnets are aligned side-by-side to the other magnets. The axis of each of the magnets is perpendicular to the bed and in other embodiments, the axis can be parallel to the axis of the other magnets and perpendicular to the channels.

In another embodiment, the plurality of magnets are arranged in alternating magnetic poles so that the magnets are aligned side-by-side with a configuration of north-south-north-south, or are slightly offset from the side-by-side configuration.

In yet another embodiment, the plurality of magnets are vertically aligned in alternating poles so that there is a vertical line of north poles aligned side-by-side with a vertical line of south poles, or are slightly offset from the side-by-side configuration.

In still another embodiment, the plurality of magnets are horizontally aligned in alternating poles so that there is a horizontal line of north poles aligned side-by-side with a horizontal line of south poles, or are slightly offset from the side-by-side configuration.

In a further embodiment, the magnets are arranged so that one magnet having one pole is surrounded by other magnets of opposing poles on four sides.

In one embodiment of the invention, each of the channels has varying widths and the channel width is increased at an entrance near the inlet and the channel width is tapered at an exit near the outlet. The plurality of magnets can be situated underneath the channel near the inlet and the outlet of the separation chamber. The bed can be tilted on one side in relation to the separation chamber. The tilted side of the bed is in contact with one side of the separation chamber and the untilted side of the magnetic bed is from about 0.5 to about 3 cm in distance from the separation chamber.

In another embodiment, the magnetic apparatus can further comprise a switching mechanism for bringing the separation chamber in contact with the plurality of magnets and the magnetic bed thereby activating the magnetic field produced by the magnets, or for distancing the separation chamber from the plurality of magnets and the bed thereby deactivating the magnetic field. The switching mechanism can be a plurality of guide rails and electromagnetic coils, rack and pinions or belt driven.

The mixture of chemical entities can be a whole blood sample and the components can be any biological micromolecules such as red blood cells, white blood cells, platelets and other plasma borne components.

The present invention provides a magnetic system having a multi-dimensional gradient for continuous, on-line separation of blood components from whole blood. The system comprising: (a) at least one mixing chamber for agitating a blood sample and magnetic particles, the particles being attached to a blood component of the blood sample upon agitation, and (b) at least one separation chamber. The separation chamber comprises a plurality of magnets and a plurality of channels having an inlet and an outlet. The magnets are arranged on one side of the channels and are in contact with one another to create a magnetic field. The blood samples containing the particle attached blood components are introduced into the inlet of the channels of the separation chamber, and the magnetic field of the magnets captures the particle attached blood components within the channels and the remaining blood sample exits the outlet of the channels of the separation chamber.

In another embodiment of the invention, the magnetic system further comprises a solution reservoir for introducing solution through the inlet and the channels for flushing out the particle attached blood components through the outlet of the channels of the separation chamber upon deactivation of the magnetic field. The magnetic system comprises a decoupling agent reservoir for introducing a decoupling agent to the particle attached blood components and an additional mixing chamber for agitating the decoupling agent and the particle attached blood components allowing the separation of the particle and the components. In one embodiment, the decoupling agent attaches to the blood components and the magnetic particle to deattach. The decoupling agent attached blood components and microspheres mixture are reintroduced into the separation chamber and the magnets are reactivated to produce the magnetic field which captures the particles and the remaining decoupling agent/blood components exit the outlet of the channel of the separation chamber. The decoupling agent can either be physical such as pressure and temperature or chemical such as sugar, salt or pH changes.

The magnetic system can also comprise a treatment device for treating the remaining blood sample; a collection chamber for reintroducing the blood components to the remaining blood sample; and a plurality of directional valves for controlling the flow of the blood sample, blood components, solutions and decoupling agent.

The channels can have numerous shapes including serpentine configurations. In one embodiment, each of the channels has varying widths, and the channel width is increased at an entrance near the inlet and the channel width is tapered at an exit near the outlet. The plurality of magnets can also be situated underneath the channel near the inlet and the outlet of the separation chamber. The bed can be tilted on one side in relation to the separation chamber. The tilted side of the bed is in contact with one side of the separation chamber and the untilted side of said bed being from about 0.5 to about 3 cm in distance from the separation chamber.

The present invention also provides a magnetic apparatus having a multi-dimensional gradient for separation of blood components from whole blood. The apparatus comprises a separation chamber comprising a plurality of magnets and a plurality of channels having an inlet and an outlet. The magnets are arranged on one side of the channels and are in contact with one another to create a magnetic field. A blood sample containing magnetic particle attached blood components is introduced into the inlet of the channels of the separation chamber and the magnetic field of the magnets captures the particle attached blood components within the channels and the remaining blood sample exits the outlet of the channels of the separation chamber.

In one embodiment, the separation chamber further comprises a bed for supporting the magnets and the bed is composed of a magnetizable material such as soft iron metal.

The present invention also provides method of continuously and magnetically separating a component from a mixture of chemical entities utilizing a multi-dimensional gradient. The method comprising the steps of: a) introducing a blood sample to a plurality of magnetic microspheres; b) agitating the blood sample and microspheres and inducing the microspheres to attach to blood components of the blood sample; c) providing a separation chamber, the separation chamber comprising a plurality of magnets and a plurality of channels having an inlet and an outlet, the magnets being arranged on one side of said channels and in contact with one another to create a magnetic field; d) introducing the blood sample containing the microsphere attached blood components into the inlet and through the channels of the separation chamber; e) activating the magnets to produce a magnetic field to capture the microsphere attached blood components within the channels; and f) allowing the remaining blood sample to exit the outlet of the channels of the separation chamber.

The method can further comprise the step of (g) providing a solution reservoir and upon deactivation of the magnetic field, introducing solution through the inlet and the channels flushing out the microsphere attached blood components through the outlet. The method can also further comprise the steps of (h) introducing a decoupling agent to the microsphere attached blood components and (i) separating the magnetic particles and components using the decoupling agent, and (j) reintroducing the decoupling agent attached blood components and particles mixture into the separation chamber and reactivating the magnetic field allowing the capture of the particles and exiting of the decoupling agent attached blood components from the separation chamber. In one embodiment, the separation of the particles and the components by allowing the decoupling agent to attach to the blood components and microspheres to deattach. The method can further comprise the step of treating the remaining blood sample of step (f) and step (k) wherein the magnetic field is deactivated and solution is introduced into the inlet and through the channels flushing out the magnetic particles through the outlet.

In one embodiment, the method can further comprise the step of reintroducing the blood components to the remaining blood sample using a collection chamber and controlling the travel of the blood sample, the blood components, solutions and decoupling agent using a plurality of directional valves.

The method can also comprise the step of providing the separation chamber with a bed for supporting the magnets. The bed is preferably composed of a magnetizable material such as soft iron metal. The magnets are a high energy rare earth magnets and preferably NdFeB or SmCo magnets.

Each of the magnets has an axis with opposing north and south poles and further comprises the step of arranging the magnets so that one of the poles rests on the magnetic bed and the other pole faces the plurality of the channels and aligning each of the magnets side-by-side to the other magnets. The axis of each magnet is perpendicular to the magnetic bed. In one embodiment, the axis of each of the magnets is parallel to the axis of the other magnets and perpendicular to the channels.

In one embodiment, the method comprises arranging the magnets in alternating magnetic poles with a configuration of north-south-north-south, or slightly offset from the side-by-side configuration.

In another embodiment the method comprises the step of vertically aligning the plurality of magnets in alternating poles so that there is a vertical line of north poles aligned side-by-side with a vertical line of south poles, or slightly offset from the side-by-side configuration.

In still another embodiment, the method comprises the step of horizontally aligning the plurality of magnets in alternating poles so that there is a horizontal line of north poles aligned side-by-side with a horizontal line of south poles, or slightly offset from the side-by-side configuration.

In a further embodiment, the method comprises arranging the magnets so that one magnet having one pole is surrounded by other magnets of opposing poles on four sides.

The method can further comprise the step of varying the widths of the channels. The channel width is increased at an entrance near the inlet and the channel width is tapered at an exit near the outlet. The method can also comprise situating the plurality of magnets underneath the channel near the inlet and the outlet of the separation chamber. The method also includes tilting the bed on one side in relation to the separation chamber. The tilted side of the bed is in contact with one side of the separation chamber and the untilted side of said bed is from about 0.5 to about 3 cm in distance from the separation chamber.

The method can further comprise the step of providing a switching mechanism for bringing the separation chamber in contact with the bed and the magnets, thereby activating the magnetic field. The method can also include providing guide rails and electromagnetic coils for distancing the separation chamber and the magnets/bed thereby deactivating the magnetic field.

The present invention also provides method of manufacturing a continuous blood separating apparatus. The method comprising the steps of: a) providing a separation chamber, the separation chamber comprising a plurality of magnets and a plurality of channels having an inlet and outlet, the magnets being arranged on one side of the channels and being in contact with one another to create a magnetic field; and b) providing a bed for supporting the magnets.

BRIEF DESCRIPTION OF THE DRAWINGS

A more complete appreciation of the present invention and many of the attendant advantages thereof will be readily understood by reference to the following description when considered in connection with the accompanying drawings in which:

FIGS. 6 a–g illustrate overhead views of the various magnetic configurations of the magnetic apparatus of the present invention.

DETAILED DESCRIPTION OF THE PREFERRED EMBODIMENT

Figure 1:
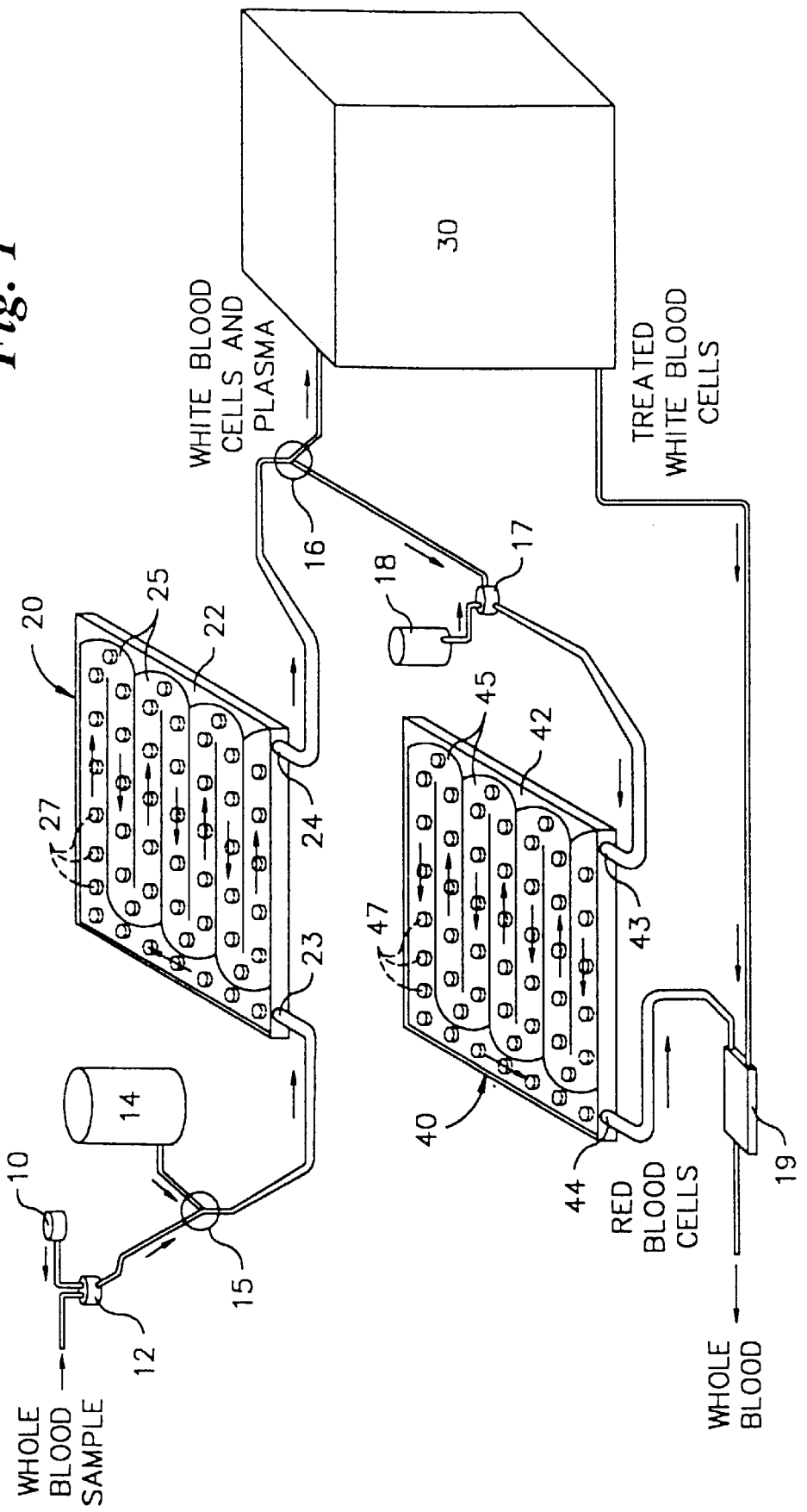
FIG. 1 illustrates a perspective view of the magnetic system of the presently claimed invention.

Referring now to the drawings wherein like reference numerals designate identical or corresponding parts throughout the several views and more particularly to FIG. 1 wherein the system and method of the present invention are illustrated. Lectin is bound to a protein covered magnetic particle such as a microsphere in mixing chamber 10 and the lectin-bound microsphere is agitated with a whole blood sample in mixing chamber 12. The agitation causes the microspheres to be bound to blood components (red blood cells) of the whole blood sample. The blood sample containing the microsphere attached blood components are then introduced into a first magnetic apparatus 20 having a separation chamber 22. The sample enters the chamber 22 through its inlet 23. The chamber 22 has a plurality of channels 25 and a plurality of magnets 27. The magnets 27 are in contact with one another. The magnets create a magnetic field and the magnetic field captures the microsphere attached blood components with the channels 25 and the remaining blood (white blood cells, platelets and plasma) travels through the channels 25 and exits the outlet 24 of the separation chamber 22.

The exiting remaining blood sample then enters a treatment device 30 such as a UVAR photophoresis system. The magnetic field is deactivated and a solution is introduced into the separation chamber 22 from a solution reservoir 14. The solution enters to inlet 23, travels through the channels 25 and flushes out the microsphere attached blood components through the outlet 24 of the separation chamber 22. The microsphere attached blood components travel through directional valve 16 and enter another mixing chamber 17 where a decoupling agent (such as sugar or salt) from the decoupling agent reservoir 18 is introduced. In mixing chamber 17, the microsphere attached blood components and the decoupling agent are agitated causing the decoupling agent to attach to the blood components and the microspheres to deattach. The decoupling agent attached blood components and microspheres mixture is introduced to a second magnetic apparatus 40 having a separation chamber 42. The mixture enters the chamber 42 through its inlet 43. The mixture flows through a plurality of channels 45 and a plurality of magnets 47 situated underneath the channels 45. The magnetic field of the magnets 47 are activated and the microspheres are captured within the separation chamber 42. The decoupling agent attached blood components travel through the channels 45 and exit outlet 44 of the chamber 42. The treated blood and blood components are then reintroduced to one another using collection chamber 19.

Figure 2:
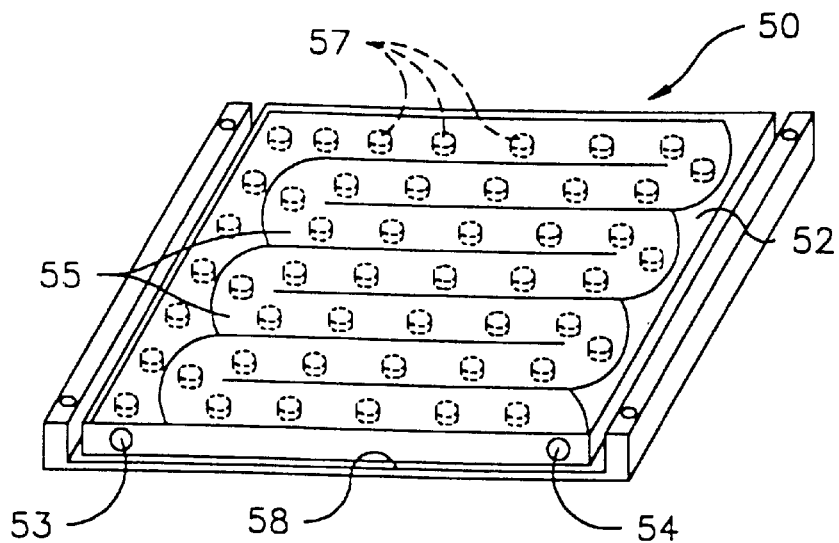
FIG. 2 illustrates a perspective view of the magnetic apparatus of the present invention.

FIG. 2 illustrates a perspective view of an assembled magnetic apparatus 50 comprising separation chamber 52 and a bed 58. The separation chamber 52 comprises a plurality of magnets 57 and a plurality of channels 55 having an inlet 53 and an outlet 54. The bed 58 can be composed of a soft iron magnetic metal. The magnets 57 are high energy rare earth magnets and preferably NdFeB or SmCo magnets. The magnets 57 have an axis with opposing north and south poles, and one of the poles rests on the magnetic bed 58 while the other pole faces the channels 55. Each of the magnets 57 are aligned side-by-side to the other magnets.

Figure 3:
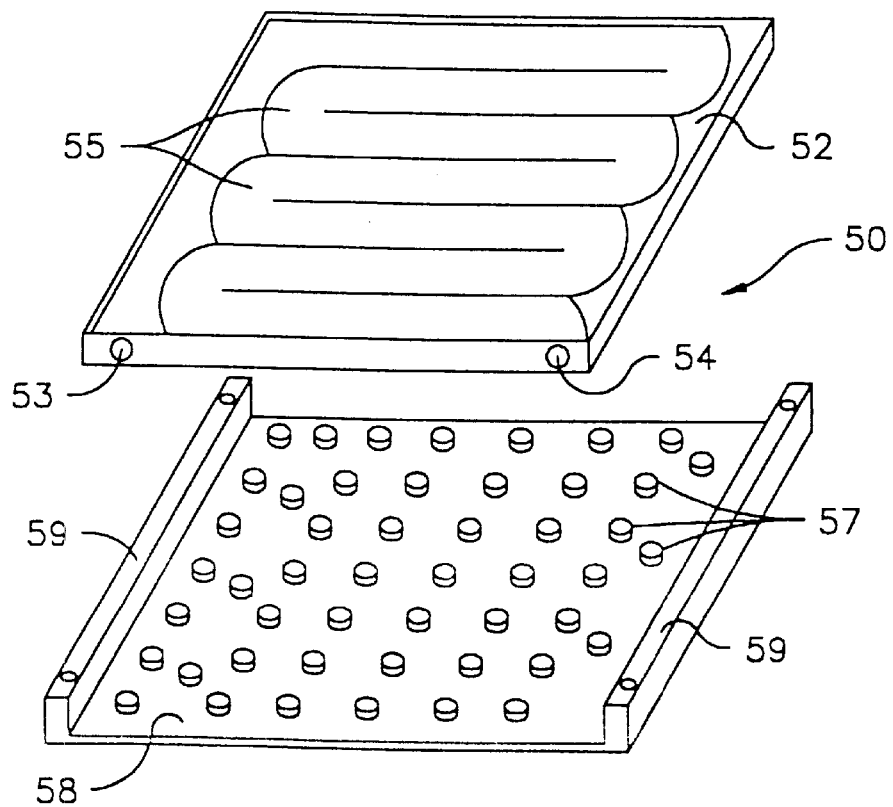
FIG. 3 illustrates a perspective view of the magnetic apparatus of the present invention including the separation chamber, the bed and the plurality of magnets.

FIG. 3 illustrates a perspective view of a disassembled magnetic apparatus 50, particularly focusing on the various components of the apparatus 50. The bed 58 has a surface upon which a plurality of magnets 57 are aligned. The bed 58 has at least two elevated edges 59 and the separation chamber 52 is set between the edges 59 of the bed 58 and above the plurality of magnets 57.

Figure 4:
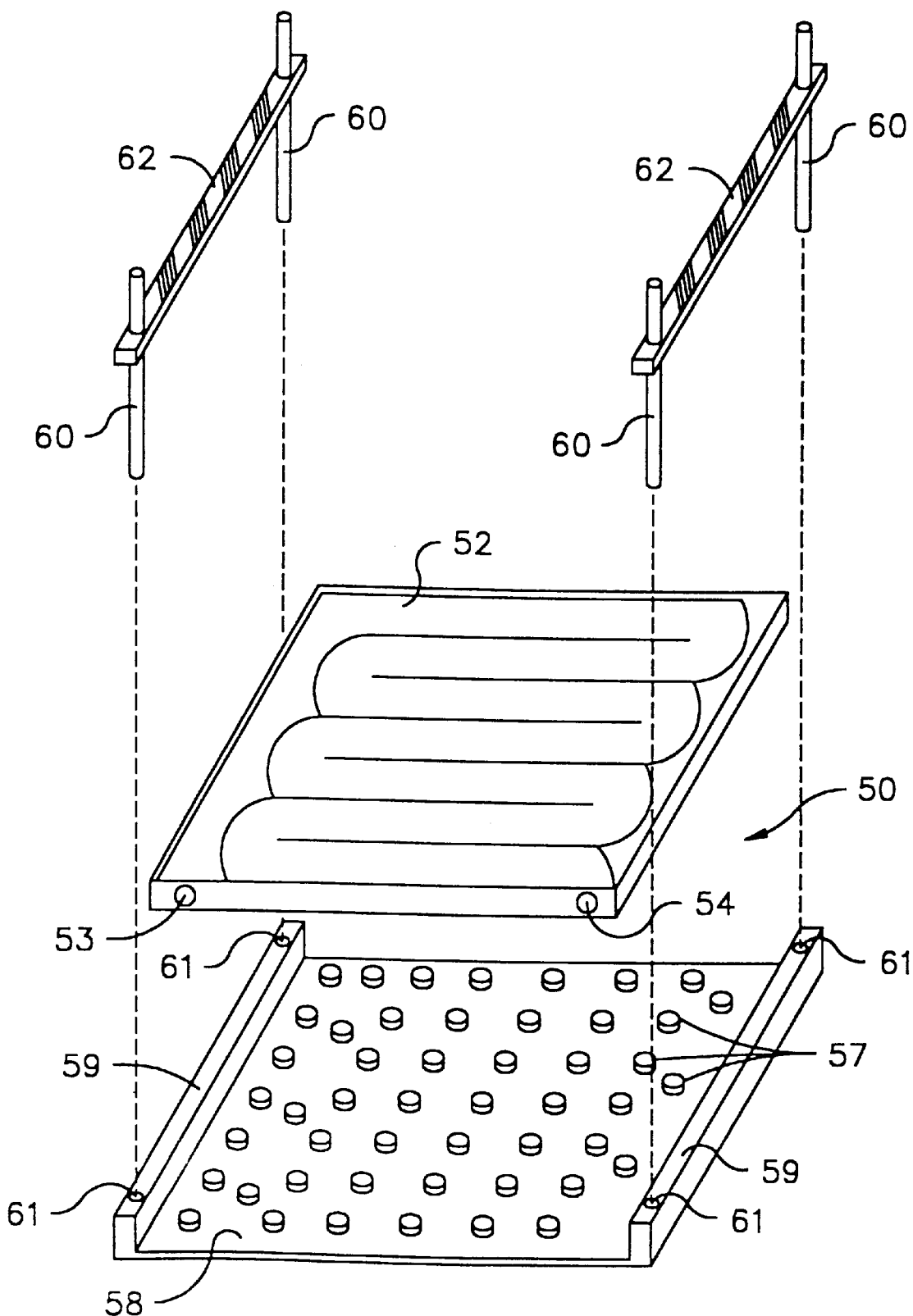
FIG. 4 illustrates a perspective view of one embodiment of the switching mechanism of the magnetic apparatus of the present invention including guide rails and electromagnetic coils.

FIG. 4 illustrates an alternate embodiment of the magnetic separation apparatus 50 of the present invention. The apparatus 50 comprises a separation chamber 52 and a bed 58. The separation chamber 52 has a plurality of channels 55 and an inlet 53 and outlet 54. The chamber 52 also has a plurality of magnets 57 situated upon the bed 58. The bed 58 has at least two elevated edges 59 and apertures 61 on the edges 59. The apparatus 50 also comprises a plurality of electromagnetic coils 62, each coil 62 having at least two guide rails 60. The coils 62 are attached to the chamber 52 and the guide rails 60 are inserted in the apertures 61 of the edges 59 of the bed 58. The coils 62 travel up and down the guide rails 60 determining the distance between the chamber 52 and the magnets 57, thereby allowing the activation and deactivation of the magnetic field of the magnetic apparatus 50.

Figure 5A:
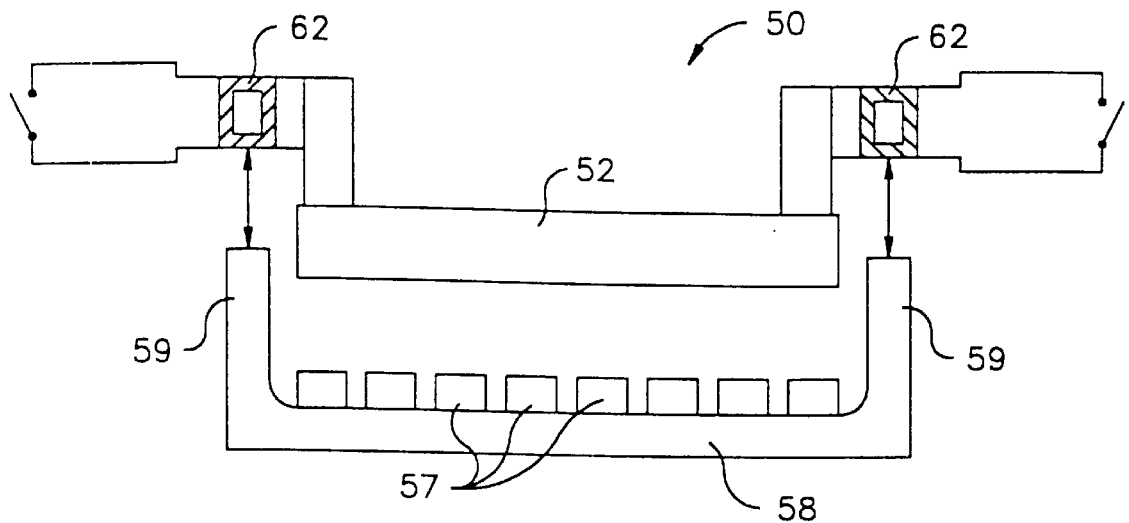
FIG. 5a illustrates a cutaway view of the magnetic apparatus with guide rails and electromagnetic coils in a de-energized state.

FIG. 5a illustrates a cutaway view of the magnetic apparatus 50 of the present invention in a de-energized or magnetic field deactivated state. The magnets 57 are set on the bed 58 which has elevated edges 59. The separation chamber 52 is connected to electromagnetic coils 62. There is a distance between the coils 62 and the edges 59 creating a distance between the chamber 52 and the magnets 57 on the bed 58.

Figure 5B:
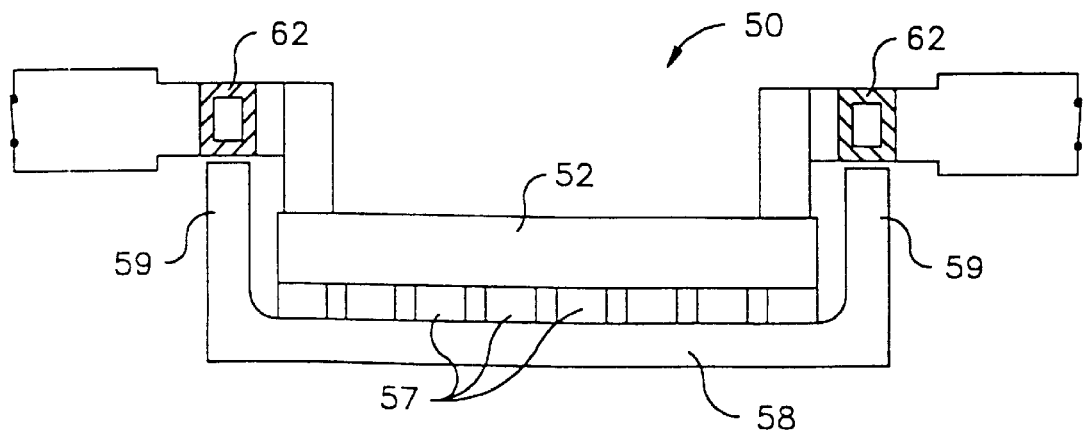
FIG. 5b illustrates a cutaway view of the magnetic apparatus in an energized state.

FIG. 5b illustrates a cutaway view of the magnetic apparatus 50 of the present invention in an energized or magnetic field activated state. The coils 62 are in contact with edges 59 thus creating contact between the magnets 57 on the bed 58.

FIGS. 6a–g illustrate various configurations of the magnets in the present invention. FIG. 6a depicts a plurality of magnets arranged in alternating magnetic poles so that the magnets are aligned side-by-side with a configuration of north-south-north-south. FIG. 6b illustrates the magnets in FIG. 6a slightly offset from the side-by-side configuration. FIG. 6c depicts a plurality of magnets vertically aligned in alternating poles so that there is a vertical line of north poles aligned side-by-side with a vertical line of south poles. FIG. 6d illustrates a plurality of magnets horizontally aligned in alternating poles so that there is a horizontal line of north poles aligned side-by-side with a horizontal line of south poles. FIG. 6e depicts a slightly offset configuration of FIG. 6d. FIG. 6f depicts a slightly offset configuration of FIG. 6c. FIG. 6g illustrates a plurality of magnets arranged so that one magnet having one pole is surrounded by other magnets of opposing poles on four sides.

Figure 7:
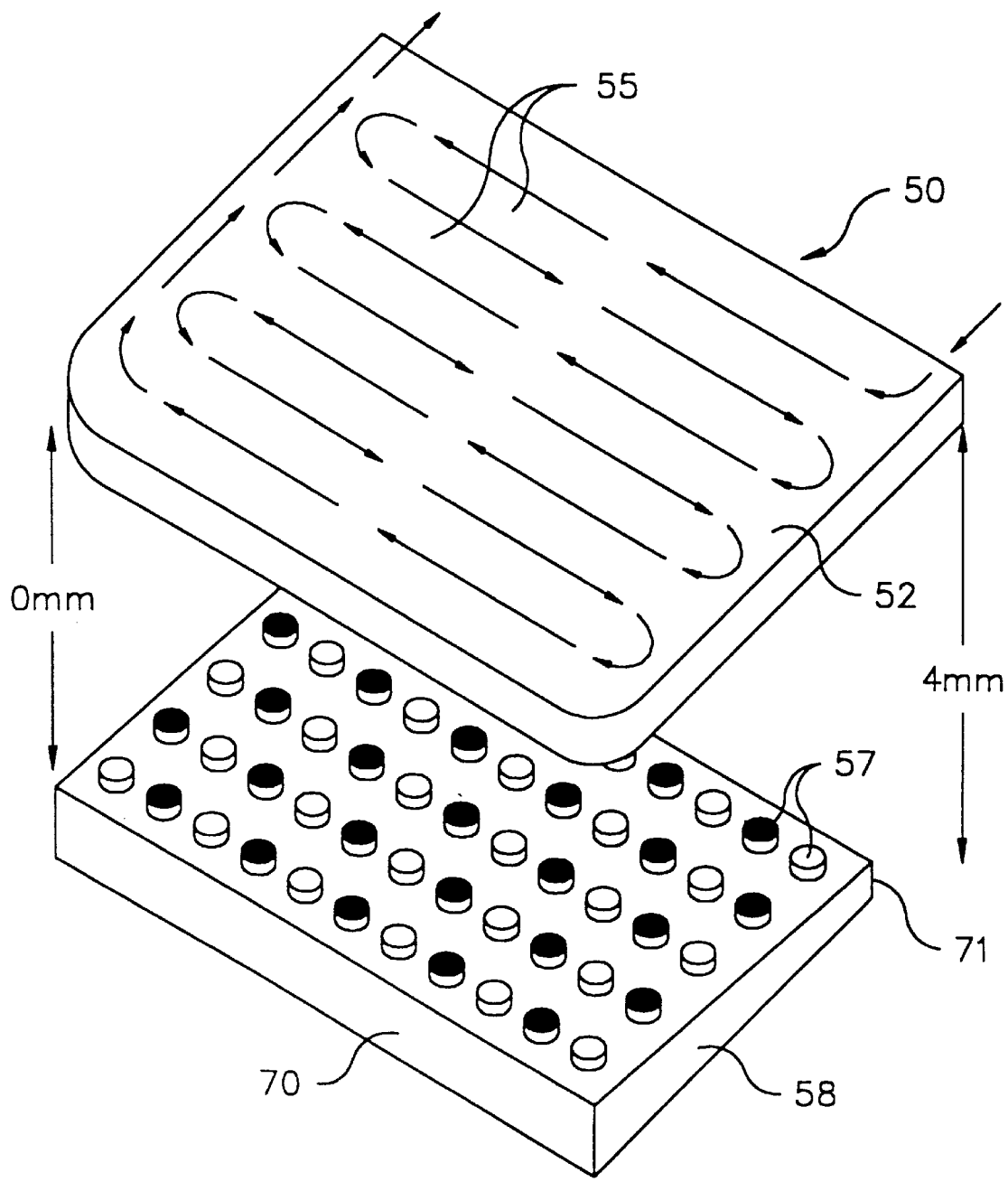
FIG. 7 illustrates a perspective view of the magnetic apparatus wherein the bed is in a tilted configuration.

FIG. 7 illustrates another embodiment of the magnetic separation apparatus 50 of the present invention wherein the bed 58 is tilted on one side 70 in relation to the separation chamber 52. The tilted side 70 of the bed 58 can be in contact with one side of the chamber 52 and the untilted side 71 of the bed 58 being from about 0.5 to about 3 cm is distance from the chamber 52.

Obviously numerous modifications and variations of the present invention are possible in light of the above teachings. It is therefore to be understood that within the scope of the appended claims hereto, the invention may be practiced otherwise than or specifically described therein.

What is claimed is:

1. A method of continuously and magnetically separating a component from a mixture of chemical entities utilizing a multi-dimensional gradient, said method comprising the steps of:

(a) introducing a mixture of chemical entities to a plurality of magnetic particles;
(b) agitating the mixture and magnetic particles and inducing the magnetic particles to attach to a component of said mixture;
(c) providing a first magnetic separation apparatus comprising:
   (1) a first separation chamber having a plurality of channels and an inlet and an outlet,
   (2) a first plurality of magnets being arranged external and to one side of said first separation chamber, said magnets being in magnetic contact with one another to create a magnetic field, and
   (3) a first switching mechanism for activating and deactivating the magnetic field produced in the first separation chamber by said magnets;
(d) introducing the mixture containing the magnetic-particle-attached component into said inlet and through said channels of said first separation chamber;
(e) activating said first plurality of magnets to produce a magnetic field to capture said magnetic-particle-attached component within said channels and thereby creating a remaining mixture; and
(f) allowing the remaining mixture to exit said outlet of said channels of said first separation chamber.

2. The method of claim 1 further comprising the step of (g) providing a solution reservoir and upon deactivation of the magnetic field, introducing solution through said inlet and said channels flushing out the magnetic-particle-attached component through said outlet.

3. The method of claim 1 further comprising the step of (h) introducing a decoupling agent to the magnetic-particle-attached component.

4. The method of claim 3 further comprising the step of (i) separating the magnetic particles from said component using the decoupling agent.

5. The method of claim 4 wherein the separation of said component and the magnetic particles is caused by the decoupling agent attaching to said component and causing the magnetic particles to deattach.

6. The method of claim 4 further comprising the steps of:
(j) providing a second magnetic separation apparatus comprising:
   (1) a second separation chamber comprising a plurality of channels and having an inlet and an outlet,
   (2) a second plurality of magnets being arranged external to and on one side of said separation chamber, said magnets being in magnetic contact with one another to create a magnetic field, and
   (3) a second switching mechanism for activating and deactivating the magnetic field produced in said separation chamber by said magnets;
(k) introducing the separated component and said magnetic particles into said inlet and through said channels of said second separation chamber;
(l) activating said second plurality of magnets to capture the magnetic particles; and
(m) allowing the remaining mixture containing said separated component to exit said outlet of said channels of said second separation chamber.

7. The method of claim 6 wherein said second magnetic separation apparatus and said first magnetic separation apparatus are one and the same apparatus.

8. The method of claim 3 wherein the decoupling agent is sugar.

9. The method of claim 3 further comprising the step of controlling the flow of the mixture, the remaining mixture and decoupling agent.

10. The method of claim 6 further comprising the step of (k) deactivating said magnetic field and introducing solution through said inlet and said channels flushing out said magnetic particles through said outlet.

11. The method of claim 1 further comprising the step of treating the remaining mixture of step (f).

12. The method of claim 11 further comprising the step of recombining said separated component with the remaining mixture of step (f) using a collection chamber.

13. The method of claim 1 comprising the step providing said first separation chamber with a bed for supporting said first plurality of magnets.

14. The method of claim 13 wherein said bed is composed of a magnetizable soft iron metal.

15. The method of claim 1 wherein each of said first plurality of magnets has opposing north and south poles, said axis of each of said first plurality of magnets being perpendicular to said bed.

16. The method of claim 15, wherein said axis of each of said first plurality of magnets being parallel to said axis of the other of said first plurality of magnets and perpendicular to said channels.

17. The method of claim 15 further comprising the step of arranging said first plurality of magnets so that one of said poles rests on a top surface of said bed and the other pole faces said plurality of channels and aligning each of said magnets in a side-by-side configuration to the other said first plurality of magnets.

18. The method of claim 15 further comprising the step of arranging said magnets in alternating magnetic poles with a configuration of north-south-north-south.

19. The method of claim 17 wherein said first plurality of magnets are slightly offset from said side-by-side configuration.

20. The method of claim 15 further comprising the step of tilting said bed on one side in relation to said separation chamber.

21. The method of claim 20 wherein said tilted side of said bed is in contact with one side of said separation chamber and an untilted side of said bed being from about 0.5 to about 3 cm in distance from said separation chamber.

22. The method of claim 15 further comprising the step of having the first switching mechanism bring said separation chamber in contact with said bed and said first plurality of magnets thereby activating the magnetic field produced by the first plurality of magnets and separating said separation chamber from said first plurality of magnets and said bed thereby deactivating the magnetic field.

23. The method of claim 13 further comprising the step of vertically aligning said first plurality of said magnets in alternating poles so that there is a vertical line of north poles aligned in a side-by-side configuration with a vertical line of south poles.

24. The method of claim 23 wherein said first plurality of magnets are slightly offset from the side-by-side configuration.

25. The method of claim 13 further comprising the step of horizontally aligning said first plurality of said magnets in alternating poles so that there is a horizontal line of north poles aligned in side-by-side configuration with a horizontal line of south poles.

26. The method of claim 25 wherein said first plurality of are slightly offset from said side-by-side configuration.

27. The method of claim 13 further comprising the step of arranging said first plurality of magnets so that one of said first plurality of magnets is surrounded by other of said first plurality of magnets of opposing poles on four sides.

28. The method of claim 1 further comprising the step of varying the widths of the channels, said channel width is increased at an entrance near said inlet and said channel width is tapered at an exit near said outlet.

29. The method of claim 1 further comprising the step of situating said first plurality of magnets underneath said at least one of said channels near said inlet and said outlet of said separation chamber.

30. The method of claim 1 wherein the magnetic particle is a microsphere that is ligand covered and coupling agent bound.

31. The method of claim 30 wherein the ligand is a protein and the coupling agent is lectin.

32. The method of claim 1 wherein said component is selected from the group consisting of red blood cells, white blood cells, platelets and plasma borne components.

33. The method of claim 1 wherein said component comprises red blood cells.

34. The method of claim 1 wherein said component comprises white blood cells.

35. The method of claim 1 wherein the mixture of chemical entities is a whole blood sample.

* * * * *